(12) United States Patent
Contijoch et al.

(10) Patent No.: US 10,588,511 B2
(45) Date of Patent: Mar. 17, 2020

(54) NON-CARTESIAN RETROSPECTIVE RECONSTRUCTION OF CARDIAC MOTION IN PATIENTS WITH SEVERE ARRHYTHMIA

(71) Applicant: The Trustees of The University of Pennsylvania, Philadelphia, PA (US)

(72) Inventors: Francisco Contijoch, San Diego, CA (US); Walter R. T. Witschey, Philadelphia, PA (US); Robert C. Gorman, Lower Gwynedd, PA (US); Yuchi Han, Philadelphia, PA (US); Joseph H. Gorman, III, Lower Gwynedd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 704 days.

(21) Appl. No.: 15/304,176

(22) PCT Filed: Apr. 24, 2015

(86) PCT No.: PCT/US2015/027543
§ 371 (c)(1),
(2) Date: Oct. 14, 2016

(87) PCT Pub. No.: WO2015/164761
PCT Pub. Date: Oct. 29, 2015

(65) Prior Publication Data
US 2017/0035298 A1 Feb. 9, 2017

Related U.S. Application Data

(60) Provisional application No. 61/984,275, filed on Apr. 25, 2014.

(51) Int. Cl.
*A61B 5/00* (2006.01)
*A61B 5/055* (2006.01)
(Continued)

(52) U.S. Cl.
CPC .......... *A61B 5/0044* (2013.01); *A61B 5/055* (2013.01); *A61B 5/7289* (2013.01);
(Continued)

(58) Field of Classification Search
USPC ......................................................... 463/413
See application file for complete search history.

(56) References Cited

U.S. PATENT DOCUMENTS

| 5,997,883 A * | 12/1999 | Epstein | G01R 33/5673 |
| | | | 324/306 |
| 2009/0232379 A1* | 9/2009 | Kohler | G06T 7/20 |
| | | | 382/131 |

(Continued)

OTHER PUBLICATIONS

Bacharach et al., "Comparison of fixed and variable temporal resolution methods for creating gated cardiac blood-pool image sequences", J Nucl Med, Jan. 1990, 31(1), 38-42.

(Continued)

*Primary Examiner* — Pierre E Elisca
(74) *Attorney, Agent, or Firm* — BakerHostetler (57) ABSTRACT

A retrospective reconstruction method uses cardiac self-gating for patients with severe arrhythmias. Self-gated myocardial systolic and diastolic motion is determined from low-spatial and high-temporal resolution images and then the MRI-dataset is retrospectively reconstructed to obtain high quality images. The method uses undersampled image reconstruction to obtain the low-spatial and high-temporal resolution images, including those of different beat morphologies. Processing of these images is utilized to generate a cardiac phase signal. This signal allows for arrhythmia detection and cardiac phase sorting. The cardiac phase signal allows for detection of end-systolic and diastolic events which allows for improved sampling efficiency. In the case of frequent and severe arrhythmia, the method utilizes data (Continued)

from the normal and interrupted beats to improve sampling and image quality.

12 Claims, 6 Drawing Sheets

(51) Int. Cl.
    *G01R 33/567*     (2006.01)
    *G01R 33/48*     (2006.01)
    *G01R 33/561*     (2006.01)
    *G01R 33/56*     (2006.01)

(52) U.S. Cl.
    CPC ..... *G01R 33/4824* (2013.01); *G01R 33/5614* (2013.01); *G01R 33/5676* (2013.01); *A61B 2576/023* (2013.01); *G01R 33/5608* (2013.01); *G01R 33/5611* (2013.01)

(56) References Cited

U.S. PATENT DOCUMENTS

| | | | |
|---|---|---|---|
| 2012/0243756 A1* | 9/2012 | Samsonov | G01R 33/56509 382/131 |
| 2016/0169999 A1* | 6/2016 | Herza | A61B 5/055 600/411 |
| 2017/0169564 A1* | 6/2017 | Hansen | G01R 33/5611 |
| 2018/0140216 A1* | 5/2018 | Li | A61B 5/055 |
| 2018/0306882 A1* | 10/2018 | Li | G06K 9/36 |

OTHER PUBLICATIONS

Contijoch et al., "The spatial and temporal fidelity in real-time MRI in patients with sinus rhythm and arrhythmias", Journal of Cardiovascular Magnetic Resonance, Jan. 16-19, 2014, 1-2.

Fessler et al., "Nonuniform Fast Fourier transforms using min-max interpolation", IEEE Trans on Signal Process, Feb. 2003, 51, 560-574.

Hansen et al., "Retrospective reconstruction of high temporal resolution CINE images from real-time MRI using Iterative motion correction", Magn Reson Med, Sep. 2012, 68, 741-750.

Jackson et al., "Selection of a convolution function for Fourier inversion using gridding computerized tomography application", IEEE Trans Med Imaging, Sep. 1991, 10, 473-478.

Muthurangu et al., "Real-time Assessment of Right and Left Ventricular Volumes and Function in Patients with Congenital Heart Disease by Using High Spatiotemporal Resolution Radial k-t Sense", Radiology, 2008, 248, 817.

Pruessmann et al., "Advances in sensitivity encoding with arbitrary k-space trajectories", Magn Reson Med., 2001, 46, 638-651.

Walsh et al., "Adaptive reconstruction of phased array MR imagery", Magn Reson Med., 2000, 43, 682-690.

Winkelmann et al., "An optimal radial profile order based on the Golden Ration for time-resolved MRI", IEEE Trans Med Imaging, 2007, 26, 68-76.

Witschey et al., "Real-Time Magnetic Resonance Imaging Technique for Determining Left Ventricle Pressure—Volume Loops", Ann. Thorac. Surg., May 2014, 97, 1597-1603.

Xue et al., "High spatial and temporal resolution retrospective cine cardiovascular magnetic resonance from shortened free breathing real-time acquisitions", Journal of Cardiovascular Magnetic Resonance, Nov. 14, 2013, vol. 13, pp. 3,4 and 6.

Yushkevich et al., "User-guided 3D active contour segmentation of anatomical structures: Significantly improved efficiency and reliability", NeuroImage, 2006, 31, 1116-1128.

Zhu et al., "Region Competition: Unifying Snakes, Region Growing, and Bayes/MDL for Multiband Image Segmentation", IEEE Trans on Pattern Anal Mach Intell, 1996, 18, 34 pages.

* cited by examiner

NON-CARTESIAN RETROSPECTIVE RECONSTRUCTION OF CARDIAC MOTION IN PATIENTS WITH SEVERE ARRHYTHMIA

CROSS-REFERENCE TO RELATED APPLICATIONS

The present application is a National Stage Application filed under 35 U.S.C. 371 of International Application No. PCT/US2015/027543, filed Apr. 24, 2015, which claims priority to U.S. Provisional Application No. 61/984,275, Apr. 25, 2014, the entire contents of which are hereby incorporated by reference.

GOVERNMENT RIGHTS

This invention was made with government support under grant numbers HL103723, HL108157, and HL007954 awarded by the National Institutes of Health. The government has certain rights in the invention.

TECHNICAL FIELD

The invention relates to the development of imaging methods for patients with cardiovascular arrhythmias and, in particular, an image based method to determine the phase of cardiac motion in an image and to retrospectively reconstruct images of higher resolution.

BACKGROUND

Figure 1:
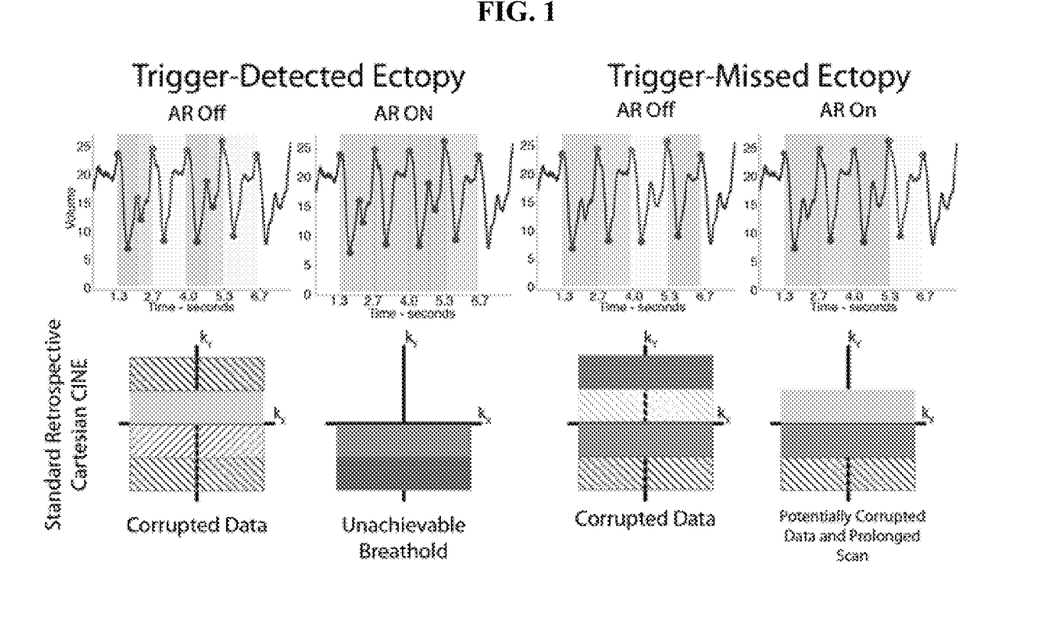
FIG. 1 illustrates failure modes for EKG-based retrospective reconstruction in the prior art.

Cardiovascular magnetic resonance imaging (MRI) is the gold standard for assessment of cardiac function but image quality is compromised in patients with severe arrhythmias. The retrospective CINE technique is standard for clinical cardiac MRI. In this technique, a fast MRI sequence is coordinated with retrospective ECG gating to synthesize data from multiple heartbeats into a single beat representing the composite cardiac motion. Using this technique, numerous short time frames are evenly produced in the cardiac cycle. However, the CINE technique is limited when imaging patients with cardiac arrhythmias. FIG. 1 illustrates several failure modes of this ECG-based retrospective reconstruction. If ectopic beats are detected by the trigger mechanism, there are two possible outcomes. If arrhythmia rejection (AR) is off, then the ectopic beats will be incorrectly scaled to the desired retrospective reconstruction (RR) duration leading to corrupt imaging data (crosshatch pattern). If AR is on, data will be rejected leading to prolonged scan times and unachievable breath holds. If the ectopic beats go undetected, k-space data will be acquired during the ectopic beats and will either be scaled, rejected, or a combination leading to imaging artifacts.

Real-time MRI methods cannot generate images with temporal and spatial resolution comparable to a multi-shot or segmented data acquisition since acquisition of MRI data is slow relative to cardiac motion. However, low-spatial and high-temporal resolution images can provide useful information about the cardiac phase. A method to utilize these images for improved retrospective reconstruction is presented.

SUMMARY

The invention addresses the above-mentioned and other needs in the art by providing a retrospective reconstruction method using cardiac self-gating for patients with severe arrhythmias. Self-gated myocardial systolic and diastolic motion is determined from low-spatial and high-temporal resolution images and then the same dataset is retrospectively reconstructed to obtain high quality images. The golden angle radial trajectory may be used in an exemplary embodiment; however, the method applies to any approach that allows for low-resolution/undersampled images to be generated at a high temporal resolution, such as spiral, radial, or other images reconstructed from a non-Cartesian sampling trajectory in k-space. The effectiveness of the method to image normal and ectopic rhythms has been evaluated and validated in patients with severe ventricular arrhythmia.

The invention includes a method whereby low-spatial and high-temporal resolution images are reconstructed to obtain cardiac information. This is done by acquiring MRI data which can be reconstructed in an undersampled manner with high temporal resolution. This dataset is then processed to determine the cardiac phase corresponding to each MRI sample. Determination of cardiac phase, in one embodiment, can be obtained by image segmentation of the left ventricle to obtain an estimation of ventricular volume. The cardiac phase estimate allows for arrhythmia detection and cardiac phase sorting. This signal also allows for detection of end-systolic and diastolic events. In the setting of severe cardiovascular arrhythmia, the method of the invention utilizes this estimate of cardiac phase to accurately combine data acquired during normal and interrupted beats, improving sampling density and image quality.

An exemplary embodiment of the invention includes a method of retrospectively reconstructing moving cardiac images with high resolution. In an exemplary embodiment, the method includes the steps of:

obtaining cardiac magnetic resonance data from a subject which allows for reconstruction of low spatial resolution and high temporal resolution cardiac images;

applying image processing to the obtained low spatial resolution cardiac images to create a cardiac phase signal;

applying arrhythmia detection and cardiac phase sorting to the cardiac phase signal to estimate the types of heart beats and estimate the cardiac phase for each data sample; and applying the cardiac phase information to perform a retrospectively gated reconstruction.

In particular embodiments, the method may include the step of measuring a ventricular volume in each image using a segmentation of ventricular volume. The method also may include similar image-based measurements such as ventricular width or myocardial thickness. In addition, the method may utilize image-based similarity measurements such as cross-correlation or squared difference.

In certain embodiments, the cardiac magnetic resonance data is obtained with respect to at least two different beat morphologies from the subject, and wherein said reconstruction is performed with respect to each of said at least two different beat morphologies.

The low-spatial and high-temporal cardiac data may be obtained in accordance with a number of techniques including: using a k-space sampling trajectory that allows for the reconstruction of low-spatial and high-temporal resolution images from a subset of the data, using a golden angle radial k-space sampling trajectory by the magnetic resonance imaging device, and reconstruction of undersampled datasets. Cardiac phase information may be obtained by image segmentation of the low-spatial and high-temporal resolution images to estimate cardiac volume or by image-based metrics of the low-spatial and high-temporal resolution images to estimate cardiac phase such as image cross-correlation. Arrhythmia detection may be applied by measuring changes in duration of beats calculated from the cardiac phase signal, by measuring changes in measured maximum and minimum values calculated from the cardiac phase signal, or from MRI-derived physiologic markers such as the opening or closing of the aortic or mitral valves.

These and other characteristic features of the invention will be apparent from the following detailed description of the invention.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, devices, and systems disclosed. In addition, the drawings are not necessarily drawn to scale. In the drawings.

DETAILED DESCRIPTION OF ILLUSTRATIVE EMBODIMENTS

Certain specific details are set forth in the following description with respect to FIGS. 2-9 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

In accordance with an exemplary embodiment of the invention, non-gated golden angle radial projections were acquired in two patients with frequent ectopic beats using a balanced steady-state free precession on a 1.5 T clinical imaging system (Avanto, Siemens Healthcare, Erlangen, Germany) equipped with nominal 40 mT/m magnetic field gradients. The data was obtained using a golden angle radial trajectory and the following imaging parameters:

TE=1.4 ms,
TR=2.8 ms,
number of acquired k-space signals per radial projection=128,
FOV=340 mm×340 mm,
bandwidth=1184 Hz/pixel, and
k-space sampling according to the golden angle ($\Phi$=~111.25°).

Imaging was performed in the short axis of the left ventricle.

Figure 2:
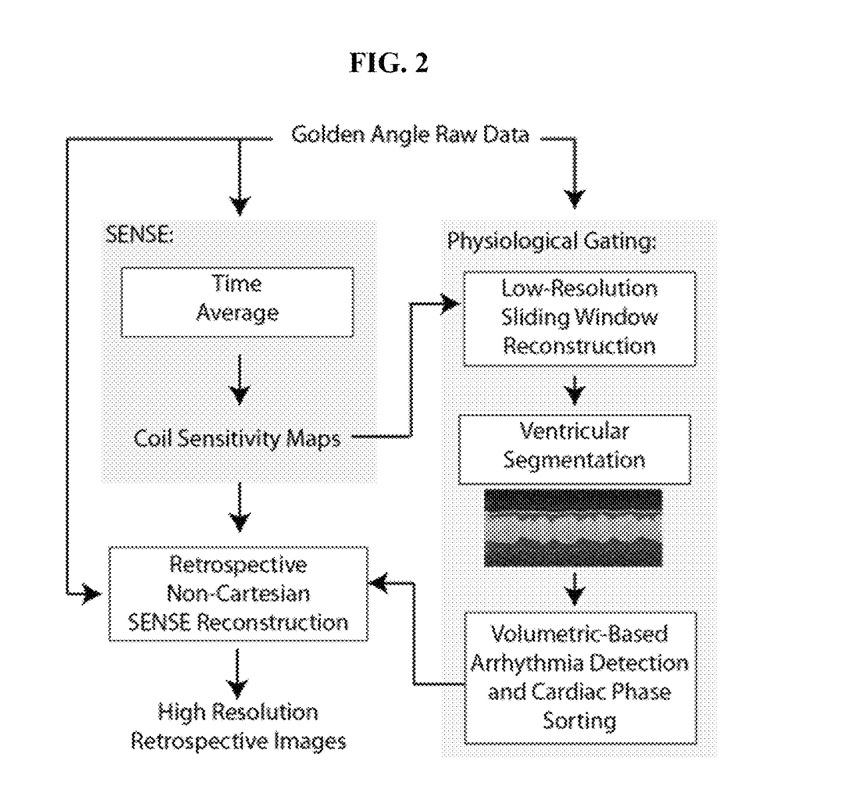
FIG. 2 illustrates a reconstruction technique in accordance with an exemplary embodiment of the invention.

FIG. 2 illustrates the reconstruction technique in accordance with an exemplary embodiment of the invention. As shown, golden angle data is used to reconstruct low spatial and high-temporal resolution images. These images are then segmented to obtain a cardiac phase signal which allows for arrhythmia detection and cardiac phase sorting. More specifically, the low spatial and high temporal resolution dataset is reconstructed using non-Cartesian SENSE algorithm with 50 radial projections per image frame and a high degree of view sharing (49 shared views per image frame). Also, the ventricular volume in each image is measured via a level-set ventricular segmentation technique to obtain a physiological gating signal. The gating signal allows for normal and ectopic systolic events to be observed using volumetric-based or temporal-based arrhythmia detection and cardiac phase sorting methods. After cardiac phase sorting, non-linear heart beat duration correction was applied to generate a retrospectively sorted dataset for high-resolution image reconstruction. As compared to ECG-based methods, the end-systolic point can be directly observed from the cardiac phase signal which allows for data from an ectopic beat to be included in the reconstruction improving scan efficiency.

Figure 3:
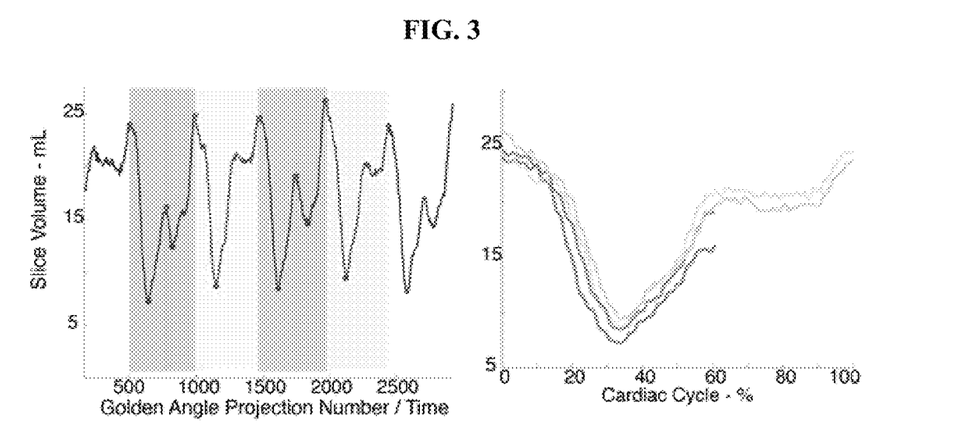
FIG. 3 illustrates the gating scheme of the invention for volumetric data from one patient and one slice with severe cardiovascular arrhythmia.

FIG. 3 illustrates the gating scheme of the invention for volumetric data from one patient and one slice with severe cardiovascular arrhythmia. In particular, FIG. 3 illustrates the reconstruction technique of the invention whereby using a left ventricular volume signal allows for detection of end-systolic and diastolic events. The left panel shows two ectopic beats (102), two normal beats (104), and two interrupted beats (106). The method of the invention utilizes data from normal and interrupted beats to improve sampling and image quality. The right panel illustrates the retrospective sorting of the volume curve, which allows for the observation of systolic and diastolic events and for the rejection of arrhythmic beats. Observation of the arrhythmic beats allows for MRI data to be more carefully 'rejected'. In particular, k-space samples do not need to be 'rejected' until the ectopic beat occurs. Knowledge of end-systole allows for data prior to arrhythmic to be included. As a result, more accurate and efficient retrospective reconstruction can be performed including, for example, variable density sampling and improved image quality prior to the occurrence of the arrhythmic beat.

Figure 4:
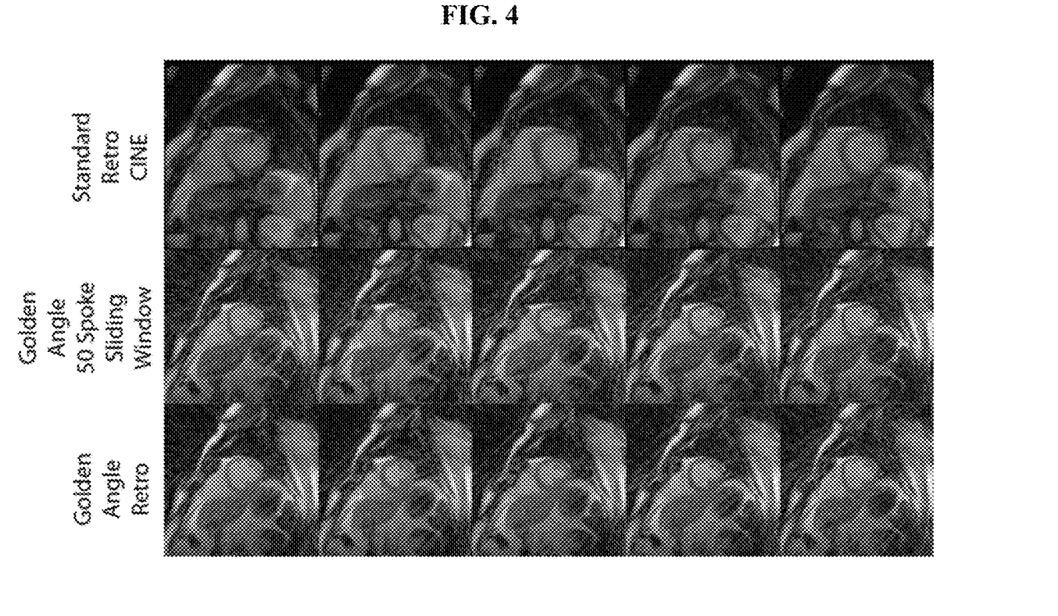
FIG. 4 illustrates the results of the reconstruction using the reconstruction technique of the invention.

FIG. 4 illustrates the results of the reconstruction for the patient. For this patient, data from all four beats is utilized to obtain high spatial and temporal resolution images. The first row illustrates standard arrhythmia corrupted images while the second row illustrates 50 spoke low spatial and high temporal resolution images for segmentation. The third row illustrates retrospective reconstructed golden angle data. Those skilled in the art will appreciate that in the two uninterrupted beats, the entire cardiac cycle is incorporated into the registration. For the beats interrupted by ectopy, the samples prior to the ectopic beat can be utilized for the retrospective reconstruction.

The reconstruction method of the invention improves upon some of the limitations of EKG-based techniques. Namely, processing of low-resolution images allows for identification of systolic and diastolic periods (both normal and ectopic). This approach allows for more efficient scanning (less discarded data). Ectopic contractions decrease the preload for subsequent beats. As a result, post-ectopic contractions are slightly different than beats prior to the ectopy. This method allows for the small changes between normal, ectopic, and post-ectopic contractions to be observed via slice volume and may allow for better cardiac phase sorting, arrhythmia rejection, and hemodynamic evaluation.

It will also be appreciated that the methods described herein may be implemented in software that operates on a processor that executes instructions stored in a memory component. The processor may include a standardized processor, a specialized processor, a microprocessor, or the like. The processor may execute instructions including, for example, instructions for implementing the method as described herein. On the other hand, the memory component stores the instructions that may be executed by the processor. The memory component may include a tangible computer readable storage medium in the form of volatile and/or nonvolatile memory such as random access memory (RAM), read only memory (ROM), cache, flash memory, a hard disk, or any other suitable storage component. In one embodiment, the memory component may be a separate component in communication with a processor, while in another embodiment, the memory component may be integrated into the processor. Such non-transitory memory components may be used as a computer readable storage device to store the instructions for implementing the methods and software features described herein.

Those skilled in the art also will readily appreciate that many additional modifications are possible in the exemplary embodiment without materially departing from the novel teachings and advantages of the invention. For example, the method may be modified to separately reconstruct or to motion correct for artifacts caused by respiratory motion. It will also be appreciated that the techniques described herein need not be limited to cardiac imaging but may also be used to provide more robust and faster imaging of patients in sinus rhythm. Also, longer scans may be used to allow for more fine-tuned selection of beats. In addition, different types of beats may be reconstructed separately. The use of image-derived measures of cardiac motion besides ventricular segmentation is intended to be included within the scope of this invention. For example, in the case of long-axis cardiac imaging, measurement of the width of the ventricle or the opening and closing of the aortic and mitral valves can be utilized to estimate cardiac phase. Furthermore, more automated measurements such as an image similarity metric can be utilized to improve the processing time of the method. Accordingly, any such modifications are intended to be included within the scope of this invention as defined by the following exemplary claims.

The present invention is illustrated by the following examples, which are not intended to limit the scope of the invention. It will be appreciated that various modifications are within the spirit and scope of the invention.

EXAMPLES

Example 1

To improve CINE MRI image quality in the presence of arrhythmias, the present inventors developed an MRI acquisition and retrospective reconstruction approach that detects and reconstructs different beat morphologies. When certain morphologies were repeatedly observed, the data was combined to provide high spatial and temporal resolution images of each beat type. The intrinsic variation of measured slice volume during sinus rhythm was quantified in volunteers and the feasibility of using the slice volume signal to reconstruct high quality images of recurring sinus beats was determined. Then, data acquired in patients with arrhythmias was successfully reconstructed. During bigeminy, multiple beat morphologies were imaged and separately reconstructed. In the presence of irregular arrhythmia, the approach allowed for improved arrhythmia rejection and improved scan efficiency.

Methods

Human Subjects

All subjects gave informed written consent. Five human subjects were imaged, three volunteers in sinus rhythm and two subjects with different rhythm disturbances: one with irregular ventricular bigeminy and one with premature ventricular contractions (PVCs).

Image Acquisition

Cardiac MRI was performed on a 1.5 T clinical imaging system (Avanto, Siemens Healthcare, Erlangen, Germany) equipped with nominal 40 mT/m magnetic field gradients, body RF transmit and a 32-channel, anterior and posterior RF receiver array. In all subjects, three short-axis slice locations were imaged at mid-ventricle.

To enable reconstruction of different beat morphologies, real-time data was collected using a 2D golden-angle radial trajectory (Winkelmann S, Schaeffter T, Koehler T, Eggers H, Doessel O. An optimal radial profile order based on the Golden Ratio for time-resolved MRI. IEEE Trans Med Imaging 2007; 26:68-76). As will be elaborated in the next section, golden angle sampling permitted multiple image reconstructions at varying spatiotemporal resolution and assured that a particular radial angle was only sampled once. These properties ensured high k-space sampling uniformity in all reconstructions, despite the presence of arrhythmias. The data was collected with the following imaging parameters, TE=1.4 ms, TR=2.8 ms, number of radial k-space data=128, FOV=220 mm-300 mm, bandwidth=1184 Hz/pixel. Consecutive k-space projections were acquired at golden angle intervals $\theta_{i+1}=\theta_i+111.25°$. After the initiation of the scan, subjects were instructed to hold their breath and then to release after a period of 15-20 seconds. In the two subjects with arrhythmias, multiple beat morphologies were observed within this time period.

As a reference, retrospective Cartesian CINE MR images were obtained using a 2D breath-held, multi-slice, retrospectively-gated, balanced steady-state free-precession sequence with the following imaging parameters, TE=1.16 ms, TR=2.32 ms, matrix=156×192, field-of-view=276 mm×340 mm, BW=930 Hz/pixel, slice thickness=8 mm, gap=2 mm and temporal resolution=21.1-35.6 ms. In subjects with rhythm disturbances, arrhythmias resulted in unachievable breath-hold durations.

Image Reconstruction

Three image reconstructions were performed from golden angle radial k-space data at different spatiotemporal resolutions to produce the final composite CINE images. The first reconstruction had high spatial resolution, the second had high temporal resolution, and the final reconstruction had both high spatial and temporal resolution. An overview of this approach is shown in FIG. 2, described supra. Golden angle radial k-space sampling was essential to permit retrospective reconstruction at different spatiotemporal resolutions and ensure highly uniform azimuthal sampling density (Winkelmann S, et al., IEEE Trans Med Imaging 2007; 26:68-76).

In the first reconstruction, for each RF detector, high signal-to-noise images were reconstructed from the entire set of acquired radial views by non-uniform fast Fourier transform with an optimized Kaiser-Bessel gridding kernel (Jackson J I, Meyer C H, Nishimura D G, Macovski A. Selection of a convolution function for Fourier inversion using gridding computerised tomography application. IEEE Trans. Med. Imaging 1991; 10:473-8; Fessler J, Sutton B. Nonuniform fast Fourier transforms using min-max interpolation. Signal Process. IEEE Trans. 2003; 51:560-574).

RF detector sensitivity profiles were then estimated from these images (Walsh D O, Gmitro a F, Marcellin M W. Adaptive reconstruction of phased array MR imagery. Magn. Reson. Med. 2000; 43:682-90). The detector sensitivity profiles served as inputs for the second image reconstruction.

In the second reconstruction, an image-based navigator was estimated from low spatial resolution, real-time motion images that were produced using a Tikhonov-regularized, non-Cartesian SENSE algorithm (Pruessmann K P, Weiger M, Bornert P, Boesiger P. Advances in sensitivity encoding with arbitrary k-space trajectories. Magn Reson Med 2001; 46:638-51) with radial projections $N_\theta$=34, temporal footprint=TR*$N_P$=95.2 ms, frame rate FR=TR (sliding window factor=1). These parameters were previously found to be sufficient to estimate continuous LV volume up to a HR=120 beats-per-minute (bpm) (Witschey W R T, Contijoch F, McGarvey J R, et al. Real-Time Magnetic Resonance Imaging Technique for Determining Left Ventricle Pressure-Volume Loops. Ann. Thorac. Surg. 2014; 97:1597-1603).

LV slice volume $V \in \mathbb{R}$ was utilized as an image-based cardiac motion navigator, estimated using a level-set segmentation technique (Yushkevich P A, Piven J, Hazlett H C, Smith R G, Ho S, Gee J C, Gerig G. User-guided 3D active contour segmentation of anatomical structures: Significantly improved efficiency and reliability. Neuroimage 2006; 31:1116-1128). First, the images were arranged in a 3D stack of size $N_x \times N_y \times N_t$, where $N_{x,y}$ were the sizes of the image spatial dimensions and $N_t$ was the total number of image frames; the typical size was 128×128×10,000. Next, binary images were generated using intensity thresh-holding. Segmentation was initialized with a propagation seed centered in the LV. 3D active contour segmentation was performed using region competition with user-defined balloon and curvature forces (Zhu S, Yuille A. Region Competition: Unifying Snakes, Region Growing, and Bayes/MDL for Multiband Image Segmentation. IEEE Trans. Pattern Anal. Mach. Intell. 1996; 18). The advantage of this arrangement was that contours between consecutive image frames were smooth, resulting in temporally consistent and smooth V of size $N_t \times 1$. Papillary muscles were automatically excluded from the segmented volume.

The image-based navigator V provided the necessary information for retrospective reconstruction, specifically, categorization of individual beats and labeling of each radial angle to the normalized cardiac phase. The navigator was segmented into individual beats $v_i \subset V$, where $i \in [1, \ldots, N]$, where N is the total number of observed beats. Beat segmentation was performed via a local maxima algorithm, which marked the beginning and end of each beat $v_i$. An input to the local maxima algorithm was the minimum change in volume $\Delta V$ lying between neighboring minima and maxima. $\Delta V$ was adjusted based on slice volume and was confirmed by visual observation of real-time images to assure detection of ectopic contractions, when present. For each beat $v_i$, cardiac phase values within the beat $cc_i$=(0, 100%] were assigned to each radial projection. To normalize cardiac phase, nonlinear temporal scaling of each beat was performed (Bacharach S, Bonow R, Green M. Comparison of fixed and variable temporal resolution methods for creating gated cardiac blood-pool image sequences. J Nucl Med. 1990 January; 31(1):38-42).

After cardiac phase determination, repeatedly observed beat morphologies $M_j \subset V$ where $j \in [1, \ldots, M]$, where M is the total number of unique beats, were determined by calculating 4 parameters for each beat $v_i$: the beat duration $RR_i$, initial slice volume $ISV_i$, minimum slice volume $MSV_i$, and final slice volume $FSV_i$. These four parameters were used to detect the occurrence of ectopic contractions, changes in loading conditions, or undesired respiratory motion. When an ectopic contraction was found to disrupt diastolic filling of a cardiac cycle, the systolic duration of the normal contraction was estimated as the time between $ISV_i$ and $MSV_i$ and used to estimate heart rate duration and re-assign cardiac phase information to projections acquired prior to the ectopic contraction.

Figure 5:
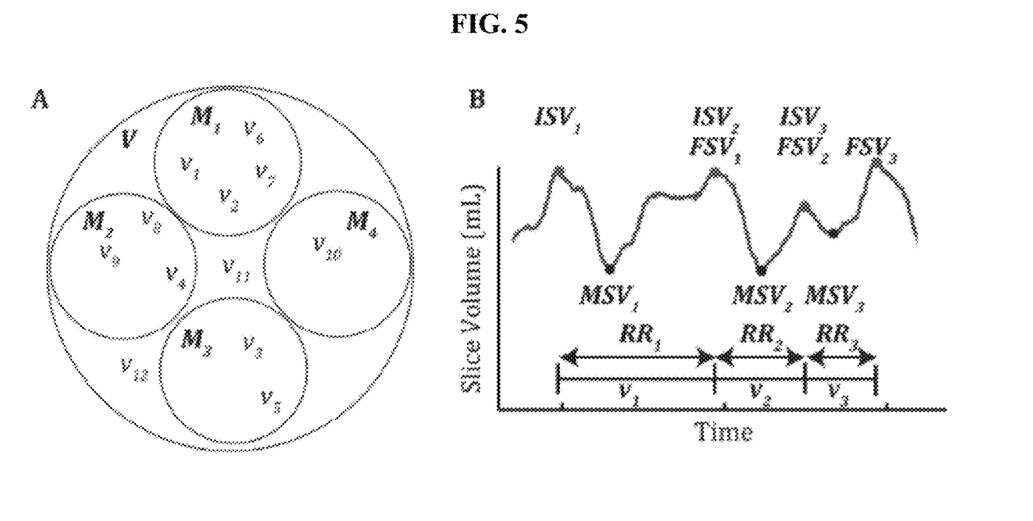
FIG. 5 depicts the segmentation of an image-based navigator V for retrospective reconstruction of multiple beat morphologies

FIG. 5 shows an example of an image-based navigator V segmented into three unique beats (labeled $v_1$, $v_2$, $v_3$) and labeled with the four navigator-derived parameters $RR_i$, $ISV_i$, $MSV_i$, and $FSV_i$. The three beats corresponded to three different morphologies $M_1$, $M_2$, and $M_3$ ($M_1$: normal contraction, $M_2$: normal contraction interrupted by an ectopic beat during diastole, $M_3$: ectopic contraction). The three morphologies were differentiated from one another using the parameters described. Specifically, $M_1$ was characterized by a long RR, high ISV, high FSV and low MSV while $M_2$ by a short RR, high ISV, low FSV and low MSV and $M_3$ by a short RR, low ISV, high FSV, and high MSV. Assignment of individual beats to a particular morphology was based on similar parameter values that were controlled via tunable tolerances.

Figure 6:
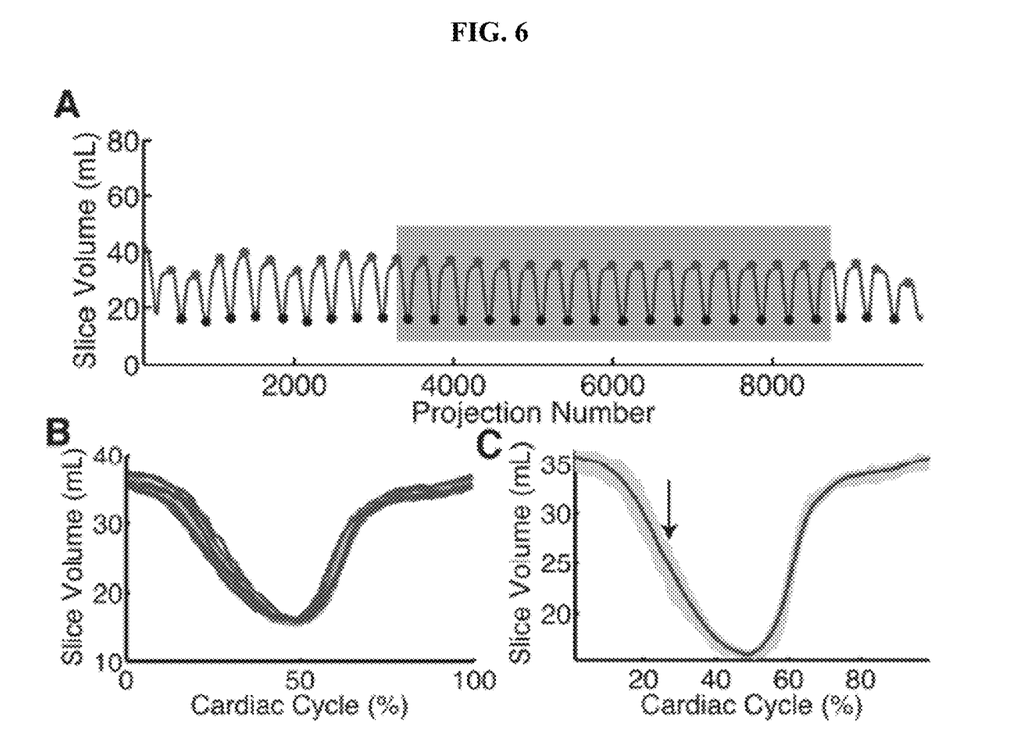
FIG. 6 shows image-based navigator V and beat selection in a normal volunteer in sinus rhythm.

The navigator V obtained from a volunteer is shown in FIG. 6A. Radial projections from accepted beats were sorted by assigned cardiac phase. The small variation in observed navigator values confirms a single beat morphology. The overlapping volume curves as well as the range of observed volume values during the breathhold are shown in FIGS. 6B and 6C.

Final images were reconstructed by binning the sorted readouts. To match typical CINE temporal resolution, 30 images were reconstructed for each beat morphology; retrospective sorting resulted in at least 100 radial spokes being binned into each image frame during a typical breathhold in sinus rhythm. As a result, minimal streaking/undersampling artifacts were observed using the iterative SENSE reconstruction.

Quantitative Analysis of Image Quality

Image quality for the proposed technique and standard CINE images was quantified using image contrast and edge sharpness (Muthurangu V, Lurz P, Critchely J D. Real-time Assessment of Right and Left Ventricular Volumes and Function in Patients with Congenital Heart Disease by Using High Spatiotemporal Resolution Radial k-t SENSE. Radiology 2008; 248). Image contrast C at end-diastole was quantified via $C=I_{LVB}/I_{SM}$ where $I_{LVB}$ is the mean intensity of a circular region of interest (ROI) in the LV blood pool and $I_{SM}$ is the mean intensity of a similarly sized ROI in the LV septal myocardium. The edge sharpness ES for each image in the cardiac cycle was calculated via ES=max(dl/dr), where dl/dr is the intensity gradient in the radial direction perpendicular to the mid-septal myocardium border. The mean and standard deviation throughout the cardiac cycle was compared among reconstruction approaches.

Statistical Analysis

A two-tailed paired Student's t-test (p<0.05) was used to detect significant differences in image contrast. Two-tailed Welch's t-test (p<0.05) was used to detect significant differences in image sharpness between the standard retrospective CINE and proposed reconstruction approach to account for the difference in variances. For patients with rhythm disturbances, a two-tailed paired Student's t-test (p<0.05) was used to detect significant differences in image sharpness over the cardiac cycle between the acquired retrospective CINE and the proposed reconstruction approach.

Results

Evaluation of Beat Volume $v_i$ Variation in Normal Subjects

To combine k-space data from multiple heartbeat morphologies, it was necessary for each type of observed rhythm morphology to be spatially consistent. It was reasoned that an acceptable level of consistency would be on the order of the beat-to-beat variation of cardiac motion in sinus rhythm during breath-holding. Since multi-shot CINE MRI combines data from multiple normal beats, the normal beat-to-beat motion variation must be sufficiently low as to produce images of acceptable quality. Therefore, real-time MRI was used to obtain images of beat-to-beat cardiac motion, quantified continuous LV volume (FIG. 6A), and then determined the motion consistency of each cardiac phase (FIG. 6B). Among the normal volunteers (N=3) in sinus rhythm, 16-18 heartbeats were collected in a single breath-hold with a mean RR-interval=877±40 ms (heart rate HR=68.5±3.2 bpm). The maximum difference in slice volume at each cardiac phase from the multiple beats was measured and the variation in measured slice volume σ was determined by the taking the fraction relative to the mean slice volume observed at each cardiac phase. At three slice locations per subject (total slices=9), $\sigma_{EDV}$=6.1%±1.6% was observed. In the normal subject shown, the maximum variation $\sigma_{V,MAX}$=22.3% was observed at 27% of the cardiac cycle (FIG. 6C, arrow).

Figure 7:
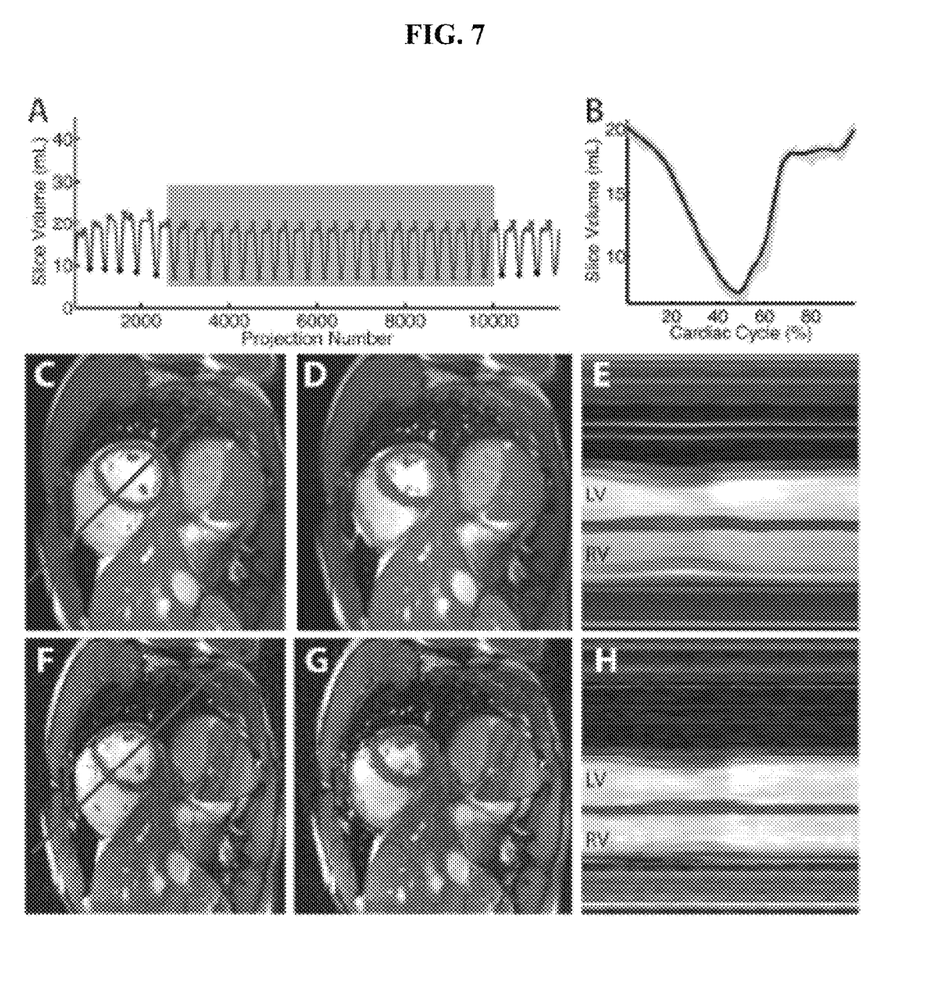
FIG. 7 illustrates an evaluation of cardiac motion consistency from a single subject in sinus rhythm.

Although the beat-to-beat variation can be sufficiently low to produce Cartesian CINE images of acceptable quality, radial sampling may be more sensitive to beat-to-beat variations because the k-space center is repeatedly sampled at each heartbeat for differences in image acquisition. To evaluate the image quality of radial sampling, 30 phases were reconstructed to match the temporal resolution of standard CINE images. The results are shown in FIG. 7. The figure illustrates image quality and spatial resolution that approximates that of the standard retrospective CINE. The variation in measured slice volume for selected beats is shown (FIG. 7B). In addition to quantifying the variability in maximum slice volume (Phase 1), it can be observed that the variation is small throughout the cardiac cycle.

Quantification of blood-myocardium contrast C and edge sharpness ES are shown in Table 1, below.

TABLE 1

| | Sinus Rhythm (N = 3) | | Bigeminy (N = 1) | | Frequent PVCs (N = 1) | |
|---|---|---|---|---|---|---|
| | CINE | Proposed Approach | CINE | Proposed Approach | CINE | Proposed Approach |
| Image Contrast | 3.91 ± 0.65 | 3.76 ± 1.23 | 2.36 | 4.62 3.29 | 2.21 | 2.93 |
| Endocardial Sharpness ^ mm$^{-1}$ | 0.11 ± 0.02 | 0.10 ± 0.02 | 0.10 ± 0.02 | 0.12 ± 0.03 0.15 ± 0.03 | 0.05 ± 0.01 | 0.10 ± 0.02 |

There was no significant difference in blood-myocardium contrast (p=0.30) between standard CINE (3.91±0.65) and the proposed reconstruction approach (3.76±1.23) in the 3 subjects in sinus rhythm (N=9). Similarly, ES showed no significant difference (p=0.56) between standard CINE images (0.11±0.02 mm$^{-1}$) and the proposed reconstruction approach (0.10±0.02 mm$^{-1}$).

Reconstruction of Beat Morphologies during Rhythm Disturbances

Imaging was performed in two subjects with rhythm disturbances. In a subject with irregular bigeminy, two different beat morphologies were repeatedly observed. The other subject had PVCs and in the setting of PVCs, the method provided improved arrhythmia rejection. In both cases, high spatial and temporal resolution image sets were generated which were void of corruptions observed in standard clinical images.

Figure 8:
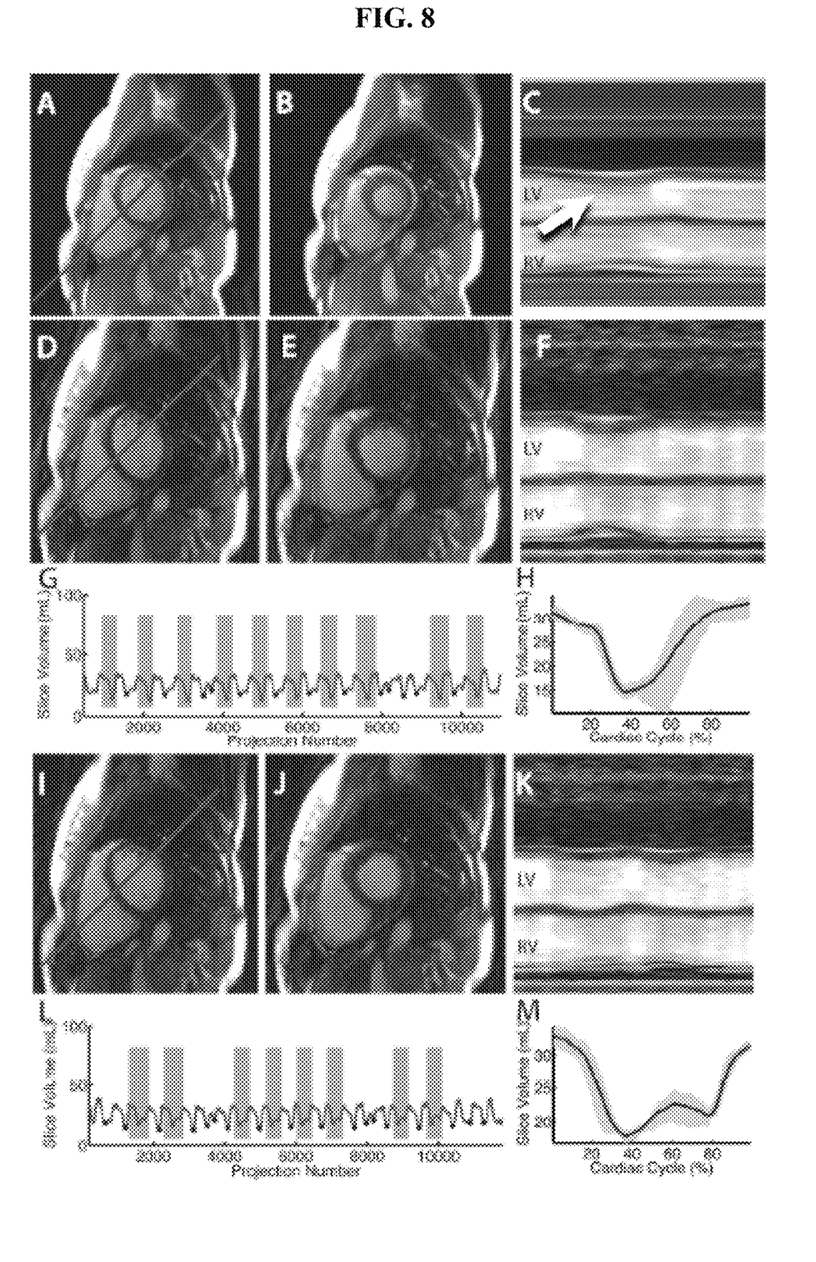
FIG. 8 depicts results obtained from a subject in irregular bigeminy.

The results obtained in a subject with irregular bigeminy are shown in FIG. 8. Subpart 8A shows end-diastole, subpart 8B shows end-systole of a scan corrupted by combination of both beat morphologies. FIG. 8C depicts a projection through the LV illustrates blurring of endocardial motion (white arrow). The proposed method allows for two beat morphologies to be reconstructed separately. The uninterrupted beat is shown in FIGS. 8D-8H while the beat that is interrupted during diastolic filling is shown in FIGS. 8I-8M. Both were generated from a breathheld acquisition. FIGS. 8F and 8K illustrate the differences in endocardial motion, which corresponds to the measured slice volume. FIGS. 8G and 8L demonstrate how desired beats can be selected from a single breathheld scan. Specifically, for this arrhythmia, separation of the morphologies was achieved using beat duration RR, initial ISV, minimum MSV, and final FSV slice volume.

Thus, during irregular bigeminy, two beat morphologies were observed: (1) an uninterrupted cardiac cycle (similar to sinus rhythm, resulting in a substantially V-shaped curve—see FIG. 8H) and (2) a cardiac cycle that is interrupted during diastole (resulting in a W-shaped volume curve—see FIG. 8M). The self-gated volume signal, derived from low-resolution MRI data, exhibited both types of heartbeats. Repetitions of the morphologies were combined to provide high spatial and temporal images of each beat morphology.

Blood-myocardium contrast C increased from the standard CINE (2.36) to the proposed reconstruction approach (4.62 and 3.29, respectively). Quantification of edge sharpness ES showed an improvement between standard CINE images (0.10±0.02 mm$^{-1}$) and the two beats reconstructed using the proposed reconstruction approach (0.12±0.03 mm$^{-1}$ and 0.15±0.03 mm$^{-1}$). In the uninterrupted beat, the increase in sharpness was not statistically significant (p=0.09), but in the interrupted beat, the increase in sharpness was highly significant p<0.0001).

In addition to reconstruction of separate beat morphologies, use of the slice volume curve as a gating signal allows for improved reconstruction of data in subjects with irregular ectopic beats. In a subject with frequent PVCs, the rhythm disturbances do not result in a repeating pattern as the PVCs occurred at different points during diastole. The volume curve allows for visualization of the maximum and minimum slice volume and this information can be utilized to estimate beat duration and appropriately scale data acquired prior to the ectopic beat. This allowed for improved scan efficiency and resulted in variable sampling density during the reconstructed images (shown in FIG. 9).

Figure 9:
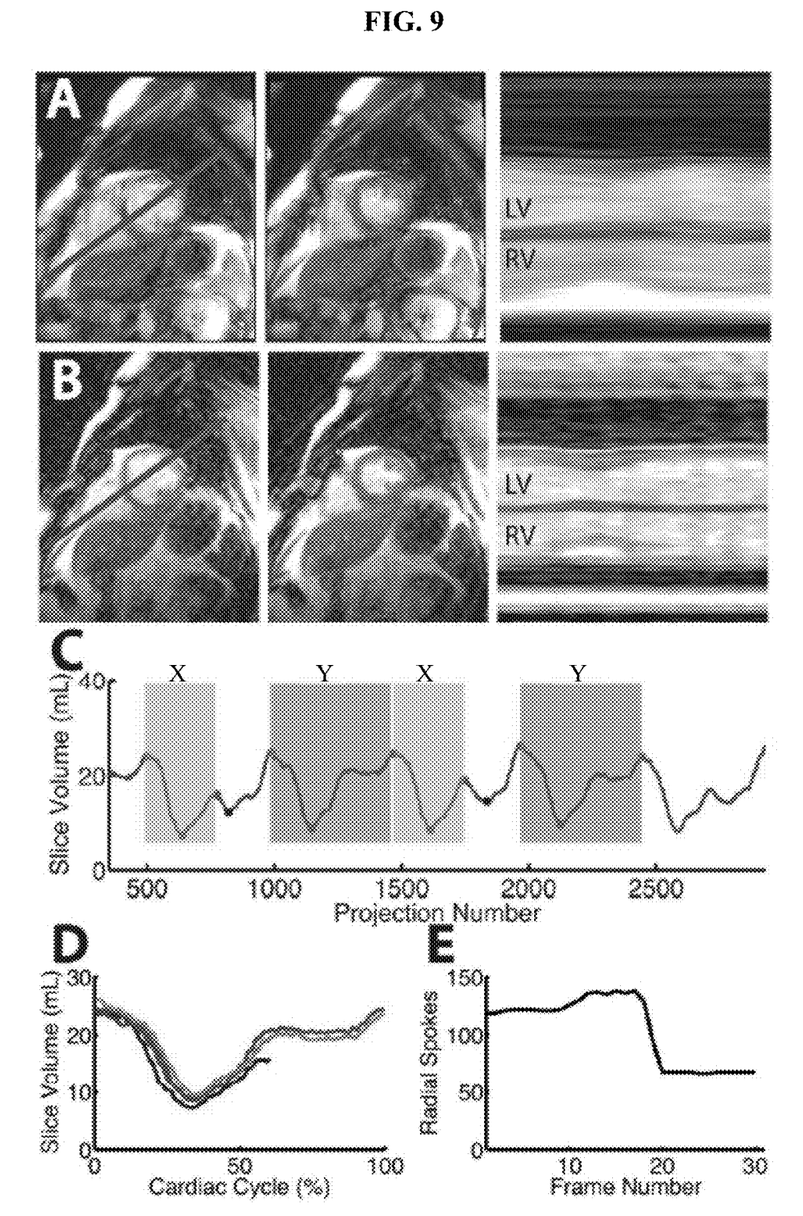
FIG. 9 pertains to a retrospective reconstruction of a subject with frequent irregular PVC.

FIG. 9A depicts how standard CINE imaging is corrupted by frequent premature ventricular contractions. FIG. 9B reveals how the instant method allows for reconstruction of images free from corruption. In FIG. 9C, a volume curve demonstrates the occurrence of PVCs, which can be excluded from reconstruction. Two uninterrupted beats are selected (boxes marked with "Y") Additional data can be introduced from timepoints prior to PVC (boxes marked with "X"). This further improves image quality. FIG. 9D shows how the overlapping volumes illustrate correct timing even for periods interrupted by PVCs. FIG. 9E shows that, based on the occurrence of the PVC in diastole, sampling density will vary among the image frames. Sampling is higher for the initial end-diastolic frame systolic periods where volumetric measurements were made.

Once again, blood-myocardium contrast C increased between standard CINE (2.21) and the proposed reconstruction approach (2.93). Edge sharpness ES showed a statistically significant (p<0.0001) improvement between corrupted standard CINE images (0.05±0.01 mm$^{-1}$) and the images reconstructed using the proposed reconstruction approach (0.10±0.02 mm$^{-1}$).

The present inventors have therefore developed an MRI method that can be used, for example, to reconstruct images of multiple heartbeat morphologies at high spatiotemporal resolution in subjects with arrhythmias. These subjects have non-periodic cardiac motion and conventional CINE MRI is usually corrupted by motion artifacts. Even when arrhythmia rejection is used to eliminate ectopic beats from data reconstruction, these images can have low quality because of inconsistent R-wave detection or beat-to-beat variations in preload. The triple radial reconstruction allows for observation of each cardiac cycle, including rhythm disturbances. The slice volume curve from high temporal resolution radial MR data can be used to detect different beats and categorize beats into various morphologies. This allows for better filtering of beat data so that only consistent data are combined during high spatiotemporal resolution image reconstruction.

In accordance with conventional methods, the beat morphology representing an arrhythmia (as in FIG. 8M) would be rejected, leading to an evaluation and diagnosis of the subject based only on the first morphology (as in FIG. 8H). The present approach, by contrast, permits the imaging of both morphologies. For example, in if imaging is performed if imaging is over x beats and a patients has y types of morphologies, images from ally morphologies can be generated. Furthermore, for each of they morphologies, if they are observed repeatedly, higher resolution images can be generated in a manner proportional to the number of repeated observations.

In the presence of arrhythmias, ECG data appears to be a poor physiologic signal to guide CINE retrospective reconstruction. Decreases were observed in quantitative measures of image quality; C decreased from 3.91±0.65 to 2.36 and 2.21 in the presence of irregular bigeminy and frequent PVCs respectively. Similarly, ES decreased from 0.11±0.02 mm$^{-1}$ in sinus rhythm images to 0.05±0.01 mm$^{-1}$ in the presence of PVCs. The image-based slice volume navigator allowed for the precise identification of normal and ectopic systolic and diastolic periods, and preload conditions. This allowed for improvements in image contrast and edge sharpness as well as more efficient scanning with less discarded data. Even in the setting of rhythm disturbances that interrupt diastole, the identification of end-systole (slice volume minimum), allowed for an estimation of the expected RR interval, phase resorting of the data, and increased sampling density prior to the rhythm disturbances as shown in FIG. 8.

The present methods permitted the observation of functional differences between normal, ectopic, and post-ectopic contractions, and this may have important clinical relevance. Since ectopic contractions affect both filling time and preload for subsequent cardiac contractions, post-ectopic contractions can be very different from beats prior to the ectopic beat. This information may be important for determination of the subject's overall cardiovascular function. Parameters such as ejection fraction or stroke volume could be defined for each type of morphology, normal, ectopic, or post-ectopic, and, when combined with information about the frequency of occurrence of that morphology, provide more detailed information about the subject's cardiac function.

Other non-Cartesian reconstruction methods have been described. Hansen, et al. recently presented a method for retrospective reconstruction of free-breathing CINE MRI data using multiple reconstructions of golden angle radial data, obtaining image-based signals of cardiac and respiratory motion and coil sensitivity maps (Hansen M S, Sorensen T S, Arai A E, Kellman P. Retrospective reconstruction of high temporal resolution CINE images from real-time MRI using iterative motion correction. Magn. Reson. Med. 2012; 68:741-50). However, instead of using image-based navigators for respiratory motion correction, the presently disclosed approach used the navigator to derive an estimate of ectopy, which can then inform the following reconstruction about cardiac motion consistency during an arrhythmia. Furthermore, it may be reasonable to obtain all three types of data (beat morphology, cardiac phase, and respiratory motion) in a single free-breathing examination. However, there are complicated relationships between thoracic pressure (during free-breathing or breath-holding), LV pressure and the ectopy occurrence and it is not entirely clear how these variables would affect image reconstruction. Altogether, these applications demonstrate the flexibility and advantageous sampling properties of radial k-space sampling compared to Cartesian CINE MRI.

In retrospective CINE MRI, the breath-hold duration is determined by the subject heart rate and scan parameters, such as the TR, phase encodes per shot (segment size) and total number of phase encodes. If the subject is unable to complete the breath-hold, substantial respiratory motion corrupts the image series. Analysis of the LV volume from image-based navigators can be used to identify the breath-hold period and any number of heartbeats can be used for retrospective reconstruction. In situations where breath-holds may not be achievable or desired, this approach should allow for reconstruction of high spatial and temporal resolution images via retrospective respiratory phase sorting. The efficiency of this approach would depend on several factors including the rate and depth of respiratory motion as well as the desired acceptance window.

In addition to retrospective CINE MRI, real-time acquisitions, driven by recent advances in multi-detector (parallel) signal detection, non-Cartesian sampling or compressed sensing reconstruction, may improve visualization of arrhythmias by providing potentially high spatiotemporal resolution scenes of every heartbeat with much less data than would be required by the Nyquist sampling criteria. Real-time MRI is ultimately limited by scanner hardware limits and safety tolerances of the human body to MR electromagnetic fields; therefore multi-beat sampling approaches will probably remain important for many applications, especially in 3D. Improvements in real-time MR are also an opportunity to enhance determination of cardiac phase or ectopy through self-gated images in the retrospective reconstruction. Triple reconstruction combines the strengths of real-time, high temporal resolution capture of inconsistent beat-to-beat cardiac motion, and retrospective CINE MRI, further enhancing spatiotemporal resolution and beat categorization.

Although the proposed method outlines the use of slice volume, other descriptive signals obtained concurrently with the acquisition or derived from real-time images can be used as a navigator to guide reconstruction. Specifically, for long-axis imaging, slice segmentation may prove more challenging than other attainable signals, since the automatic segmentation approach was not refined to prevent inclusion of the LV outflow tract or left atrium. However, with an appropriate physiologic signal, the triple reconstruction approach will result in high quality images.

What is claimed:

1. A method of retrospectively reconstructing moving cardiac images with high resolution, comprising:
   obtaining cardiac magnetic resonance data from a subject which allows for reconstruction of low spatial resolution and high temporal resolution cardiac images;
   applying image processing to the obtained low spatial resolution cardiac images to create a cardiac phase signal;
   applying arrhythmia detection and cardiac phase sorting to the cardiac phase signal to estimate the types of heart beats and estimate the cardiac phase for each data sample; and
   applying the cardiac phase information to perform a retrospectively gated reconstruction.

2. The method according to claim 1, further comprising obtaining cardiac data using a k-space sampling trajectory that allows for the reconstruction of low-spatial and high-temporal resolution images from a subset of the data.

3. The method according to claim 1, further comprising obtaining cardiac data using a golden angle radial k-space sampling trajectory by the magnetic resonance imaging device.

4. The method according to claim 1, further comprising obtaining cardiac images by reconstruction of undersampled datasets resulting in low spatial and high temporal resolution images.

5. The method according to claim 1, wherein the low spatial resolution and high temporal resolution cardiac images comprise images reconstructed from a non-Cartesian sampling trajectory ink-space.

6. The method according to claim 5, wherein the low spatial resolution and high temporal resolution cardiac images comprise images reconstructed from a spiral or radial sampling trajectory ink-space.

7. The method according to claim 1, further comprising obtaining cardiac phase information by image segmentation of the low-spatial and high-temporal resolution images to estimate cardiac volume.

8. The method according to claim 1, further comprising obtaining cardiac phase information by image-based metrics of the low-spatial and high-temporal resolution images to estimate cardiac phase such as image cross-correlation.

9. The method according to claim 1, further comprising applying arrhythmia detection by measuring changes in duration of beats calculated from the cardiac phase signal.

10. The method according to claim 1, further comprising applying arrhythmia detection by measuring changes in measured maximum and minimum values calculated from the cardiac phase signal.

11. The method according to claim 1, further comprising applying arrhythmia detection by using MM-derived physiologic markers including the opening or closing of the aortic or mitral valves.

12. The method according to claim 1 wherein said cardiac magnetic resonance data is obtained with respect to at least two different beat morphologies from said subject, and wherein said reconstruction is performed with respect to each of said at least two different beat morphologies.

* * * * *

UNITED STATES PATENT AND TRADEMARK OFFICE
CERTIFICATE OF CORRECTION

| | | |
|---|---|---|
| PATENT NO. | : 10,588,511 B2 | Page 1 of 1 |
| APPLICATION NO. | : 15/304176 | |
| DATED | : March 17, 2020 | |
| INVENTOR(S) | : Contijoch et al. | |

It is certified that error appears in the above-identified patent and that said Letters Patent is hereby corrected as shown below:

On the Title Page

On page 2, Column 2, Line 10, Item [56], References Cited, under heading OTHER PUBLICATIONS, Replace, "Muthurangu et al., "Real-time Assessment of Right and Left Ventricular Volumes and Function in Patients with Congenital Heart Disease by Using High Spatiotemporal Resolution Radial k-t Sense", Radiology, 2008, 248, 817." with --Muthurangu et al., "Real-time Assessment of Right and Left Ventricular Volumes and Function in Patients with Congenital Heart Disease by Using High Spatiotemporal Resolution Radial k-t Sense", Radiology, 2008, Vol. 248, No. 3, pp. 782-791.--

In the Specification

Column No. 3, Line no. 33, Replace, "morphologies" with --morphologies.--

In the Claims

Under Claim no. 12, Under Column no. 14, Line no. 32, Replace, "The method according to claim 1 wherein said cardiac" with --The method according to claim 1, wherein said cardiac--

Under Claim no. 11, Under Column no. 14, Line no. 29, Replace, "applying arrhythmia detection by using MM-derived physiologic" with --applying arrhythmia detection by using MRI-derived physiologic--

Signed and Sealed this
Second Day of June, 2020

Andrei Iancu
*Director of the United States Patent and Trademark Office*